(12) United States Patent
Bottlang et al.

(10) Patent No.: US 8,740,903 B2
(45) Date of Patent: Jun. 3, 2014

(54) METHOD AND APPARATUS FOR BONE FRACTURE FIXATION

(75) Inventors: Michael Bottlang, Portland, OR (US); Steven M. Madey, Lake Oswego, OR (US); Marcus Mohr, Portland, OR (US)

(73) Assignee: DePuy Synthes Products, LLC, Raynham, MA (US)

( * ) Notice: Subject to any disclaimer, the term of this patent is extended or adjusted under 35 U.S.C. 154(b) by 161 days.

(21) Appl. No.: 11/351,364

(22) Filed: Feb. 9, 2006

(65) Prior Publication Data

US 2007/0213727 A1 Sep. 13, 2007

(51) Int. Cl.
*A61B 17/72* (2006.01)

(52) U.S. Cl.
USPC .............. 606/63; 606/283; 606/905

(58) Field of Classification Search
USPC .............. 606/60, 62–64, 67, 68, 283–285
See application file for complete search history.

(56) References Cited

U.S. PATENT DOCUMENTS

| | | | | |
|---|---|---|---|---|
| 4,055,172 A | * | 10/1977 | Ender et al. | 606/62 |
| 4,327,715 A | | 5/1982 | Corvisier | |
| 4,503,847 A | * | 3/1985 | Mouradian | 606/64 |
| 4,794,919 A | * | 1/1989 | Nilsson | 606/65 |
| 5,092,889 A | | 3/1992 | Campbell, Jr. | |
| 5,201,733 A | | 4/1993 | Etheredge, III | |
| 5,443,466 A | | 8/1995 | Shah | |
| 5,766,218 A | | 6/1998 | Arnott | |
| 6,355,042 B2 | | 3/2002 | Winquist et al. | |
| 6,379,359 B1 | * | 4/2002 | Dahners | 606/62 |
| 6,527,775 B1 | * | 3/2003 | Warburton | 606/62 |
| 6,706,046 B2 | * | 3/2004 | Orbay et al. | 606/69 |
| 6,730,090 B2 | * | 5/2004 | Orbay et al. | 606/62 |
| 6,926,720 B2 | * | 8/2005 | Castaneda | 606/98 |
| 2002/0143337 A1 | | 10/2002 | Orbay et al. | |
| 2005/0085819 A1 | | 4/2005 | Ellis et al. | |
| 2005/0085824 A1 | | 4/2005 | Castaneda | |
| 2006/0085000 A1 | * | 4/2006 | Mohr et al. | 606/69 |
| 2007/0083202 A1 | * | 4/2007 | Eli Running et al. | 606/62 |

FOREIGN PATENT DOCUMENTS

| | | |
|---|---|---|
| JP | 3-168145 | 7/1991 |
| JP | 10-85231 | 4/1998 |
| JP | 2003-265494 | 9/2003 |
| JP | 2005-527316 | 9/2005 |
| WO | WO 87/04612 A1 | 8/1987 |
| WO | WO 03/101320 | 12/2003 |
| WO | WO 2005/072284 A2 | 8/2005 |

OTHER PUBLICATIONS

Moore, Bryan P., "Operative stabilization of non-enetrating chest injuries," The Journal of Thoracic and Cardiovascular Surgery, vol. 70, No. 4, Oct. 1975, pp. 619-627.
Paris et al., "Surgical stabilization of traumatic flail chest," Thorax, 1975, 30, pp. 521-527.
Schupbach et al., "indikationen zur Rekonstruktion des instabilen Thorax bei Rippenserienfrakturen und Ateminsuffizienz," Helv. chir. Acta, 1976, 43, pp. 497-502.
Meier et al., "Zur Therapie des instabilen Thorax bei Reppenserienfrakturen," Schweiz. med. Wschr. 108, Nr. 16, 1978, pp. 608-613.

* cited by examiner

*Primary Examiner* — Ellen C Hammond
(74) *Attorney, Agent, or Firm* — Baker & Hostetler LLP

(57) ABSTRACT

Embodiments of the present invention provide a method and apparatus for fixing bone with an osteosynthesis splint. In embodiments of the present invention, a splint may be introduced into a bone at a fracture site, or may enter the rib at an opening near a fracture site and extend along the intramedullary canal across the fracture site.

26 Claims, 5 Drawing Sheets

METHOD AND APPARATUS FOR BONE FRACTURE FIXATION

TECHNICAL FIELD

Embodiments of the present invention relate to the field of orthopedics, more specifically, to a method and apparatus for bone fracture fixation.

BACKGROUND

Chest wall fractures, and in particular, fractures of rib bones of the rib cage, may cause potentially life-threatening respiratory insufficiencies, accounting for up to 50% of the mortality in thorax injuries. Fractures of a rib bone may occur at any location along the bone. However, the most critical fractures often involve multiple fractures of each of a set of adjacent rib bones. In particular, if four or more consecutive rib bones of the rib cage each sustain two or more fractures, for example, to create a column of bone fragments flanked by fracture sites, the fracture pattern is referred to as a flail chest injury. In flail chest injury, a fractured region of the chest wall is detached from the remainder of the chest wall, and no longer held in position by the rib cage. Accordingly, this fractured region may move independently of the chest wall during respiration, resulting, for example, in insufficient ability for respiration.

Flail chest injury may be treated non-operatively or operatively to restore the anatomy and physiological function of the chest wall. Non-operative treatment generally involves aggressive pain control and mechanical ventilation. As a result, non-operative treatment has been associated with prolonged stays in the hospital and increased mortality rates. Operative treatment generally involves reducing and stabilizing rib fractures with surgical fixation devices (osteosynthesis hardware), such as metallic struts, plates or wires. Operative stabilization of flail chest injuries, such as with struts, plates, or wires, may provide significant benefits over non-operative treatment. For example, operative stabilization may reduce the need for, and thus the mortality associated with, prolonged mechanical ventilation. In addition, operative stabilization may dramatically reduce pain during respiration, yield faster fracture healing, prevent persistent respiratory compromise, and reduce cost for treatment.

As early as 1958, intramedullary pinning with stainless steel pins was introduced to stabilize rib fractures by inserting a thin plate in the intramedullary canal across the fracture site, see Moore, B.P., Operative stabilization of non-penetrating chest injuries, J. Thorac. Cardiovasc. Surg., 70, 619-639 (1975), the entire disclosure of which is hereby incorporated by reference. In other approaches, surgeons have inserted stainless steel (Kirschner) wires inside the ribs for rib fracture fixation. However, these thin, round wires provide little torsional stability, and may migrate over time.

In 1975, Paris et al. reported the use of stainless steel struts of three distinct sizes, which provided greater torsional stability, see Paris, F., et al., Surgical stabilization of traumatic flail chest, Thorax, 30, 521-527 (1975), the entire disclosure of which is hereby incorporated by reference. These struts were used either as an intramedullary nail inside a rib or as an external brace for application on a rib surface. For external bracing, such struts utilized a series of holes to accommodate strut fixation with suture wires.

Other fixation mechanisms have been utilized, such as the Judet plate and the Vecsei plate, but are configured exclusively for external fixation of rib fractures. In 1972, Rehbein plates were introduced, which combine internal and external fixation strategies, see Meier, P., et al., Zur Therapie des instabilen Thorax bei Rippenserienfrakturen, Schweiz. Med. Wschr., 108:606-613 (1978), the entire disclosure of which is hereby incorporated by reference. A Rehbein plate is a thin, straight, flexible plate, which is angled at the end that remains outside the bone. For insertion of a Rehbein plate, an access hole may be drilled through the outer cortex of a rib several centimeters in front of the fracture. Through this access hole, the Rehbein plate may be inserted into the intramedullary canal across the fracture site, until only the angled end section of the Rehbein plate remains outside the rib. The angled end section may be folded toward the rib surface and secured, if necessary, with suture wire. However, folding of the angled segment to the rib segment may decrease the strength of the plate at the folding line. Folding of the stainless steel plate after insertion in the rib may also cause undesirable high stress in the rib, which may lead to further fracture or splitting of the rib especially in elderly patients in which ribs are thin and fragile. Furthermore, suturing the plate end to the bone is time consuming and difficult. This is especially the case, when rib fractures are located in the rear portion of the rib where thick soft tissue and muscle layers over ribs complicate or prevent access.

BRIEF DESCRIPTION OF THE DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the figures of the accompanying drawings.

DETAILED DESCRIPTION OF EMBODIMENTS OF THE INVENTION

Figure 1:
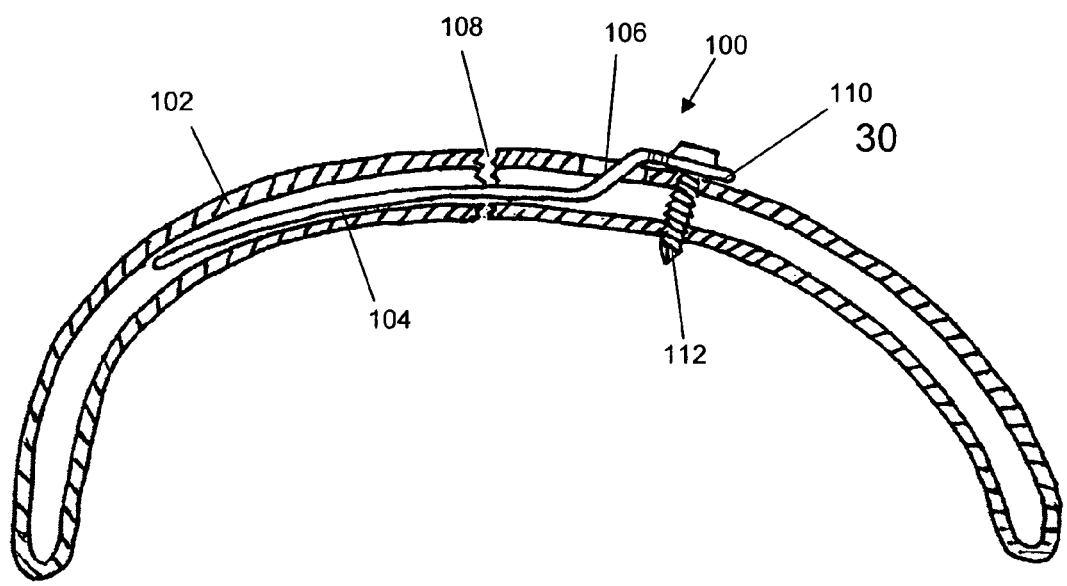
FIGS. 1, 2, 3, 4, and 5 illustrate cross-sectional views of apparatuses affixed to bone in accordance with various embodiments of the present invention.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the present invention, the phrase "A/B" means A or B. For the purposes of the present invention, the phrase "A and/or B" means "(A), (B), or (A and B)". For the purposes of the present invention, the phrase "at least one of A, B, and C" means "(A), (B), (C), (A and B), (A and C), (B and C), or (A, B and C)". For the purposes of the present invention, the phrase "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

Embodiments of the present invention provide a method and apparatus for fixing a rib with an osteosynthesis splint, which may be affixed to the outside surface of the rib on one side of the fracture, and which may extend into the intramedullary canal of the rib. In embodiments of the present invention, a splint may be introduced into a rib at the fracture site, or may enter the rib at an opening near a fracture site and extend along the intramedullary canal across the fracture site. Embodiments of the present invention may be used for fixing other bones, such as straight bones or other curved bones.

For the purposes of the present invention, the term osteosynthesis refers to a device or procedure that stabilizes and/or joins the ends of fractured bones, in part, using mechanical devices such as plates, pins, rods, splints, wires or screws.

For the purposes of the present invention, the terms "fixation" or "fixing" refers to the immobilization or stabilization of some or all of the parts of a fractured bone.

For the purposes of the present invention, the term "intramedullary" means occurring or residing within a bone, and may be used to describe, for example, devices that are completely or partially within a bone.

Embodiments of the present invention provide a method and apparatus for fixing ribs with an osteosynthesis splint. In accordance with an embodiment of the present invention, a splint may be affixed to the outside surface of a rib, for example on the anterior side of a fracture. In embodiments, an osteosynthesis splint may extend along the intramedullary canal of a rib and across the site of a fracture, or, alternatively, may be introduced at the site of a fracture.

In an embodiment of the present invention, no fixation means on the posterior side of the fracture is utilized, greatly reducing the need for surgical access to the posterior rib segments. This may not only reduce operating time, but may also reduce the amount of soft tissue dissection required for fixation of rib fractures in lateral and posterior rib segments, where thick layers of soft tissue and muscles complicate or prevent surgical access. In addition, in embodiments of the present invention, avoiding the use of additional posterior fracture fixation may allow an osteosynthesis splint of the present invention to move or flex slightly with the movement of the bone, thus avoiding unwanted additional stresses. In an embodiment of the present invention, the characteristic of the distal end of an osteosynthesis splint "floating" in the intramedullary canal of a bone avoids unwanted stresses associated with an additional posterior fixation and/or stresses conveyed back to the primary site of fixation due to tension or twisting of the splint.

FIG. 1 shows an exemplary apparatus 100 for fixing a fractured rib bone 102 with an osteosynthesis splint 104. Splint 104 may be inserted through a hole 106, created for example by drilling in the outer cortex of rib 102. In an embodiment of the present invention, for ease of insertion and access, hole 106 may be located anterior to fracture site 108. In other embodiments, hole 106 may be located posterior to fracture site 108.

In an embodiment of the present invention, to facilitate insertion of splints in a bone, a flexible reamer may be advanced through the drill hole or through a fracture site into the intramedullary canal of the bone to prepare a canal along which the osteosynthesis splint may be advanced.

In an embodiment, a splint may be advanced along the intramedullary canal in order to cross and stabilize the fracture site. As shown in FIG. 1, splint 104 may be advanced until only the securing plate segment 110 of splint 104 remains visible outside rib 102. Securing plate 110 may be secured to rib 102 using one or more fasteners, for example bone screw 112, received in corresponding holes of securing plate 11.0 and into rib 102. In addition, in FIG. 1, splint 104 extends across fracture site 108 providing stability to fracture site 108.

Embodiments of the present invention provide substantial advantages over fixation with either generic plates or intramedullary pins. For example, various embodiments of the present invention may not require access to the posterior rib segment for splint fixation, which may reduce both the operating time and the amount of soft tissue dissection during operation. Furthermore, embodiments of the present invention provide secure fixation of the osteosynthesis splint by screw fixation to prevent splint migration and fixation failure. Additional advantages of embodiments of the present invention are provided herein throughout the description.

Figure 2:
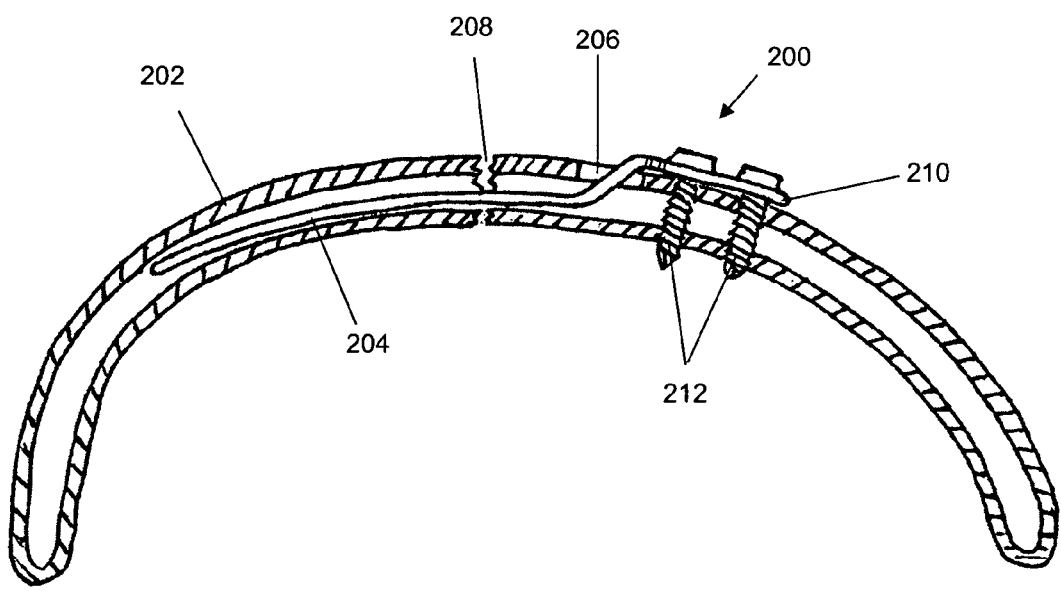

FIG. 2 shows an exemplary apparatus 200 for fixing a fractured rib bone 202 with an osteosynthesis splint 204. Splint 204 may be inserted through a hole 206, created for example by drilling in the outer cortex of rib 202 near fracture site 208. Splint 204 may be advanced until only the securing plate segment 210 of splint 204 remains visible outside rib 202. Securing plate 210 may be secured to rib 202 using a plurality of fasteners, for example bone screws 212, received in corresponding holes of securing plate 210 and into rib 202.

Bone screws 212 are shown extending through rib 202, but, in alternative embodiments of the present invention, screws may terminate in the intramedullary canal or may terminate in the bone cortex. In addition, in an embodiment of the present invention, screws may be utilized in various alignments, configurations, and/or insertion directions.

In embodiments of the present invention, fasteners other than screws may be utilized, such as pins, rods or wires. In an embodiment of the present invention, if a wire or similar fixation mechanism is utilized, a through hole in a securing plate may not be needed. Further, in embodiments of the present invention, combinations of various securing mechanisms may be utilized.

Figure 3:
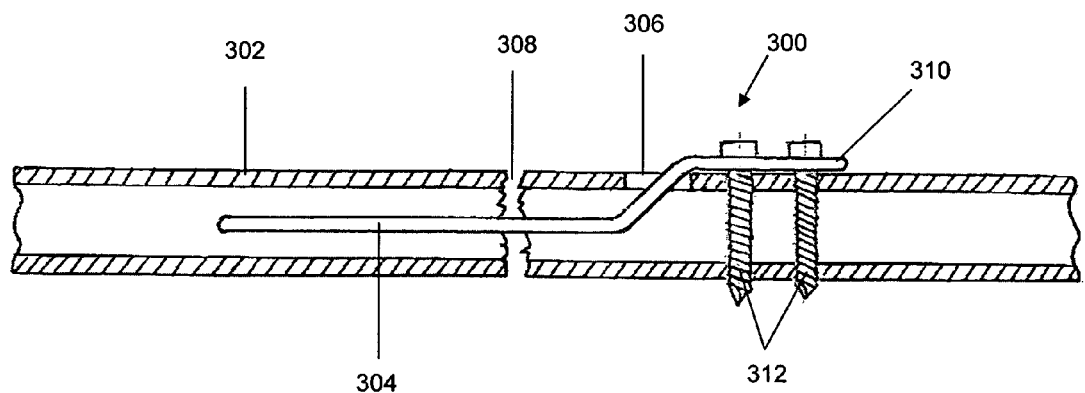

FIG. 3 shows an exemplary apparatus 300 for fixing a fractured bone 302 with an osteosynthesis splint 304. Splint 304 may be inserted through a hole 306, created for example by drilling in the outer cortex of bone 302 near fracture site 308. Splint 304 may be advanced until only the securing plate segment 310 of splint 304 remains visible outside bone 302. Securing plate 310 may be secured to bone 302 using a plurality of fasteners, for example bone screws 312, received in corresponding holes of securing plate 310 and into bone 302.

Bone 302 is representative of any of a variety of bones found in an animal body, whether straight or curved, and having a variety of cross-sections that may be fixed using an embodiment of the present invention.

Figure 4:
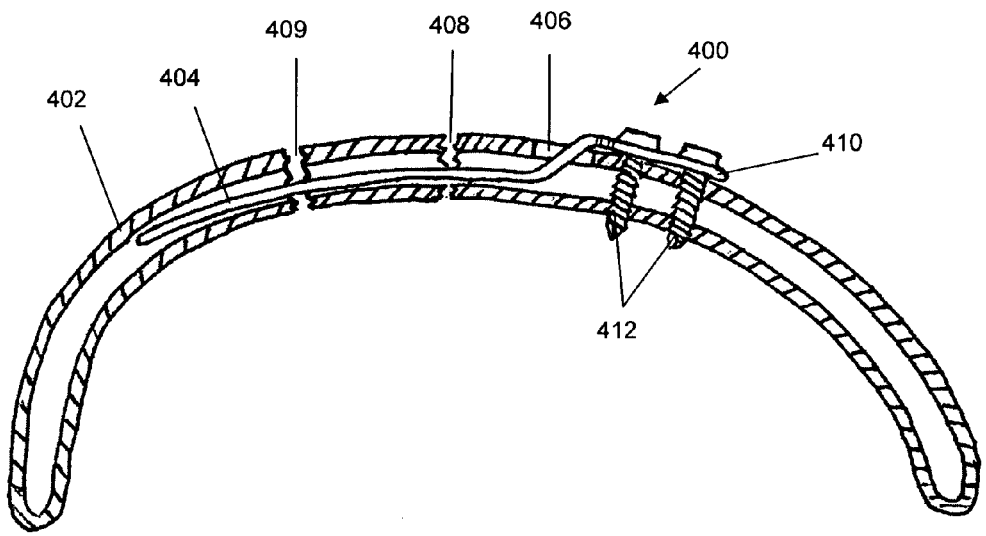

FIG. 4 shows an exemplary apparatus 400 for fixing a fractured rib bone 402 with an osteosynthesis splint 404. Splint 404 may be inserted through a hole 406, created for example by drilling in the outer cortex of rib 402 near fracture site 408. Splint 404 may be advanced until only the securing plate segment 410 of splint 404 remains visible outside rib 402. Securing plate 410 may be secured to rib 402 using a plurality of fasteners, for example bone screws 412, received in corresponding holes of securing plate 410 and into rib 402. In addition, in FIG. 4, splint 404 extends across and provides stability to fracture sites 408 and 409.

FIG. 4 shows a splint 404 being used to fix two fracture sites, but, in embodiments of the present invention, a splint may be used to fix one, two, three, or more fractures of a single bone.

Figure 5:
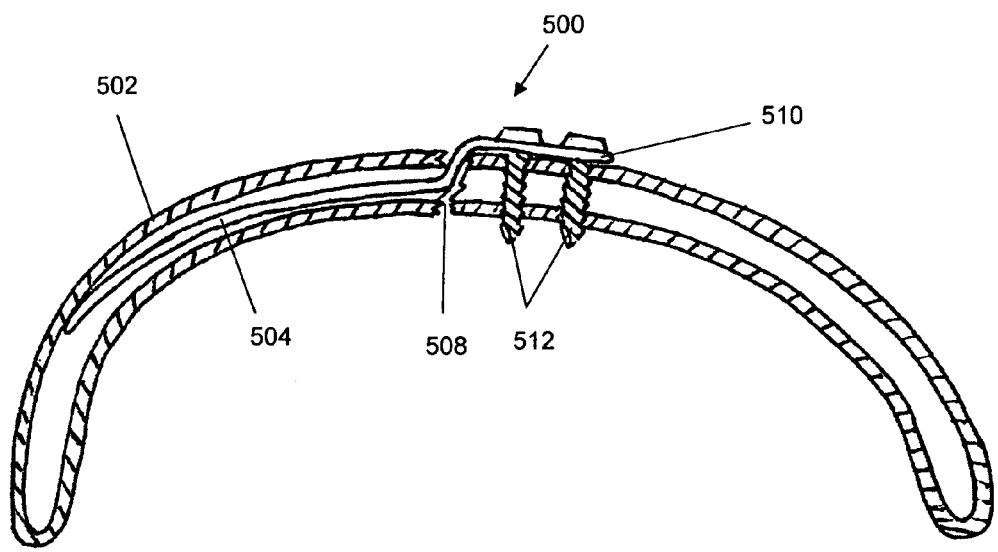

FIG. 5 shows an exemplary apparatus 500 for fixing a fractured rib bone 502 with an osteosynthesis splint 504. Splint 504 may be inserted into rib 502 at fracture site 508 thus avoiding the need for creating or using an additional insertion location. Splint 504 may be advanced until only the securing plate segment 510 of splint 504 remains visible outside rib 502. Securing plate 510 may be secured to rib 502 using a plurality of fasteners, for example bone screws 512, received in corresponding holes of securing plate 510 and into rib 502.

Figure 6:
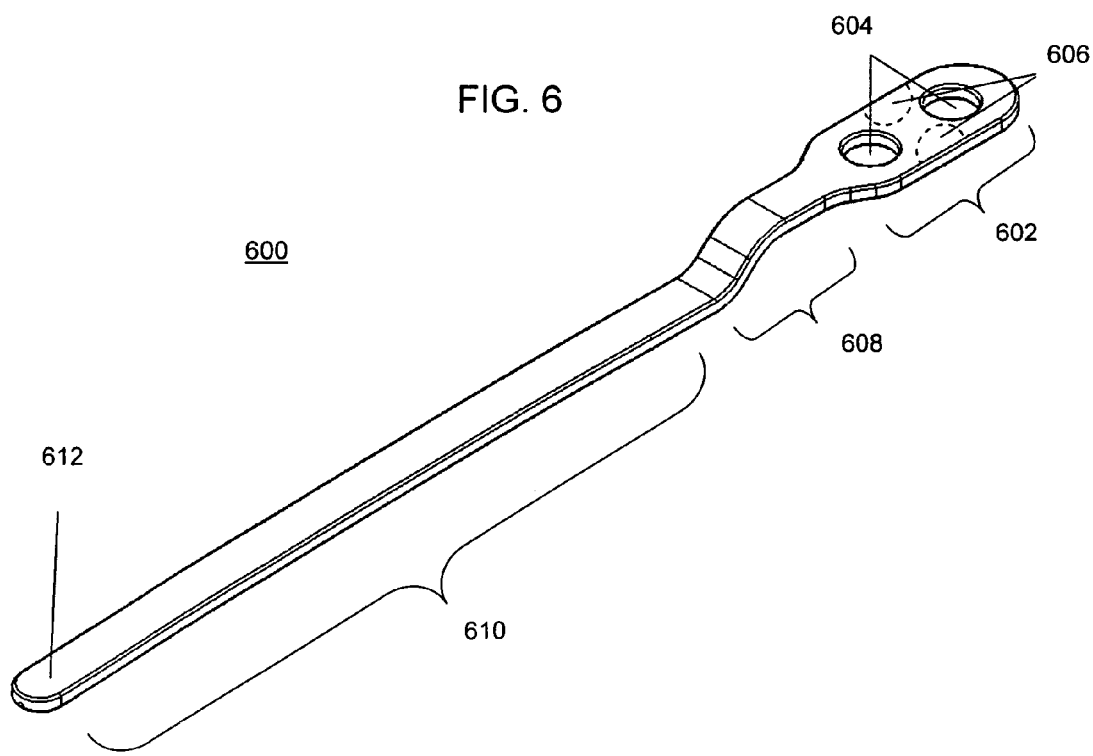
FIGS. 6 and 7 illustrate perspective views of apparatuses for fixation of bone in accordance with various embodiments of the present invention.

FIG. 6 shows an exemplary osteosynthesis splint 600 for fixing bones. Splint 600 includes a securing plate segment 602 having at least one opening 604 arranged in securing plate segment 602. In embodiments of the present invention, openings 604 may be through-holes extending through osteosynthesis splint 600. In embodiments of the present invention, each opening 604 may be threaded or nonthreaded.

In an embodiment of the present invention, securing plate segment 602 may include one or more notches 606 (shown in dashed outline) formed in securing plate segment 602. Notches 606 may be present in one or both opposing lateral edges of securing plate segment 602, and may have various shapes and sizes.

In an embodiment of the present invention, notches 606 may be utilized as a location at which to support or provide plate fixation, for example, with suture wire. In an embodiment of the present invention, notches 606 may provide a location at which to engage pliers or other gripping or insertion tool to aid in inserting splint 600 into a bone.

Splint 600 also includes transition segment 608, which provides for an offset between the plane of plate segment 602, and the plane of intramedullary segment 610. When in use, at transition segment 608, osteosynthesis splint 600 transitions from the outer surface of a bone to the intramedullary canal of the bone. Furthermore, in an embodiment of the present invention, before or at transition segment 608, the width of plate segment 602 narrows gradually to the width of intramedullary segment 610.

Transition segment 608 may have a variety of angles with respect to intramedullary segment 610, such as approximately 90°, 100°, 120°, 135° or 150°, depending on the desired application or the type or orientation of the bone to be fixed.

Splint 600 includes intramedullary segment 610, which penetrates the intramedullary canal of a bone across, and/or at, one or more fracture sites. Intramedullary segment 610 may have a circular cross-section, oval cross-section, elliptical cross-section, rectangular cross-section, or other polygonal cross-section suitable for insertion into the intramedullary canal of a bone, such as a rib bone. Distal end 612 of intramedullary segment 610 may be rounded, tapered, or pointed in order to help facilitate insertion of osteosynthesis splint 600 into a bone.

Figure 7:
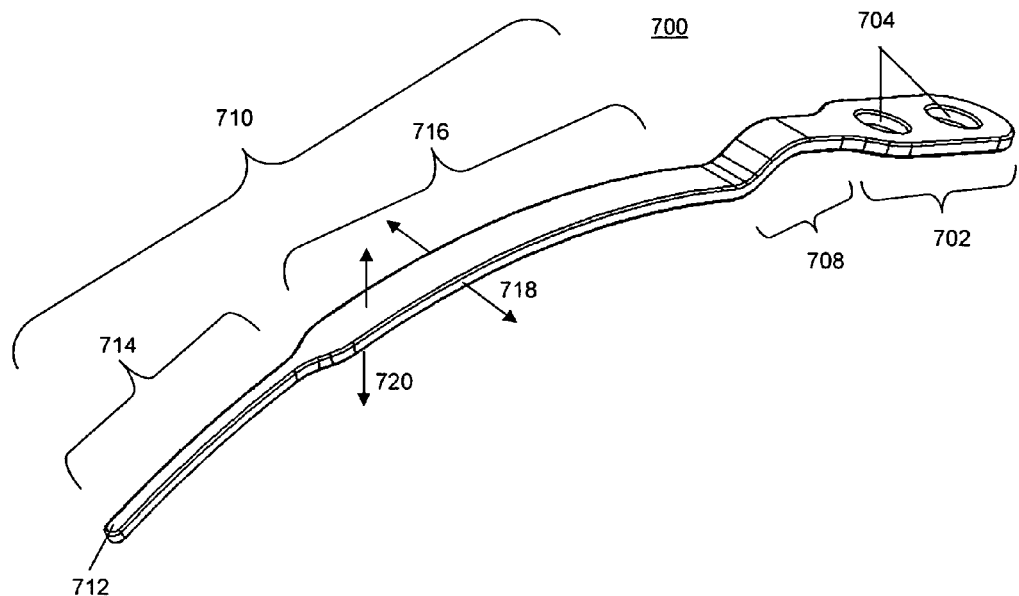

FIG. 7 shows an exemplary osteosynthesis splint 700 for fixing bones, in particular curved bones such as ribs. Splint 700 includes a securing plate segment 702 having at least one opening 704 arranged in securing plate segment 702. In embodiments of the present invention, openings 704 may be through-holes extending through osteosynthesis splint 700. In embodiments of the present invention, each opening 704 may be threaded or nonthreaded.

Splint 700 also includes transition segment 708, which connects plate segment 702 with intramedullary segment 710. When in use, in transition segment 708, osteosynthesis splint 700 transitions from the outer surface of a bone to the intramedullary canal of the bone.

Splint 700 includes intramedullary segment 710, which penetrates the intramedullary canal of a bone across, and/or at, one or more fracture sites. Intramedullary segment 710 may have a circular cross-section, oval cross-section, elliptical cross-section, rectangular cross-section, or other polygonal cross-section suitable for insertion into the intramedullary canal of a bone, such as a rib bone. Distal tip 712 of intramedullary segment 710 may be rounded, tapered, or pointed in order to help facilitate insertion of osteosynthesis splint 700 into a bone.

As shown in FIG. 7, intramedullary segment 710 includes a distal segment 714 and a proximal segment 716. Proximal segment 716 has a larger width than the width of distal segment 714. In an embodiment of the present invention, the width of proximal segment 716 may taper gradually or may transition sharply to the width of distal segment 714. In embodiments of the present invention, distal segment 714 and proximal segment 716 may have the same or different thicknesses.

In an embodiment of the present invention, distal segment 714 and/or proximal segment 716 may have substantially uniform widths along all or a portion of each segment.

In an embodiment of the present invention, distal segment 714 and proximal segment 716 possess different degrees of flexibility. In an embodiment of the present invention, proximal segment 716 is wider than it is thick, for example, in a ratio of width to thickness of about 1.5:1, 2:1, 3:1, or more, and thus possesses a higher degree of vertical flexibility (720) than lateral flexibility (718). In an embodiment of the present invention, distal segment 714 may have a width and thickness with similar dimensions, or may be constructed with either dimension larger than the other to control the flexibility characteristics. In an embodiment of the present invention, distal segment 714 has a width and thickness in a ratio of about 1:1 and thus possesses substantially uniform flexibility characteristics in all directions.

In an embodiment of the present invention, the different widths of distal segment 714 and proximal segment 716 provide for easier insertion of the splint into a bone.

In embodiments of the present invention, osteosynthesis splints may have any suitable length. The length of a securing plate segment may be sufficient for splint fixation with a single screw, or multiple screws. Exemplary lengths of a plate segment may be about 5-50 mm, for example, about 10-20 mm. Alternatively, in an embodiment of the present invention, a securing plate segment may be sufficiently long to span and stabilize a second fracture site anterior to the fracture that is stabilized with an intramedullary segment. Thus, in other embodiments of the present invention, exemplary lengths of a plate segment may be about 30-200 mm, for example, about 50-100 mm. In embodiments of the present invention, exemplary lengths for a transition segment may be about 2-10 mm, for example, about 4-8 mm. In embodiments of the present invention, exemplary lengths for an intramedullary segment may be about 20-100 mm, for example about 40-80 mm.

Segments of an osteosynthesis splint according to embodiments of the present invention may have any suitable width. For example, a plate segment may have a width of about 5-15 mm, for example 8-10 mm, such as 9 mm, among others.

In an embodiment of the present invention, an intramedullary segment, for example, may have a width of about 1-10 mm, for example 2-8 mm, such as 5 mm, among others. The width of an intramedullary segment may be substantially constant along the length of the intramedullary segment, or may vary, for example, to facilitate easier insertion, or to alter the bendability or flexibility in particular regions, or from one region to the next. For example, in an embodiment of the present invention in an intramedullary segment containing a proximal segment and a distal segment, a proximal segment may have a width of about 2-8 mm, such as 5 mm, and a distal segment may have a width of about 0.5-3 mm, such as 2 mm.

An osteosynthesis splint in accordance with embodiments of the present invention may have any suitable thickness. In an embodiment of the present invention, the thickness may be substantially constant along the length of an osteosynthesis splint, or may vary, for example, to facilitate easier insertion, or to alter the bendability or flexibility at particular regions. Exemplary thicknesses for plate segments or intramedullary segments in accordance with embodiments of the present invention may be about 0.5-3 mm.

In an embodiment of the present invention, an osteosynthesis splint may have any suitable out-of-plane curvature, such as a longitudinal curvature, or may lack a curvature. In an embodiment of the present invention, a curvature of the entire osteosynthesis splint or segments thereof may be similar to, or matched to, the curvature of a portion of a bone, such as a rib. In an embodiment of the present invention, a splint, or a segment of a splint, may have a radius of curvature of about 5-30 cm.

In an embodiment of the present invention, a plate segment may have any suitable number, orientation or configuration of openings. In embodiments of the present invention, openings may include one or a plurality of holes extending between the inner and outer surfaces of the plate segment. The holes may be disposed along the centerline of the plate segment, or off-center, staggered, or side-by-side. Furthermore, in an embodiment of the present invention, the holes may be spaced equally or non-equally. In embodiments of the present invention, the holes may be spaced apart, for example, by about 5-15 mm, for example about 10 mm. Each hole may be threaded or nonthreaded, for threaded or nonthreaded engagement, respectively, with various bone screws, pins, etc.

In embodiments of the present invention, an osteosynthesis splint may have any suitable mechanical properties. For example, in an embodiment of the present invention, a securing plate segment and/or an intramedullary segment may be configured to substantially match the strength of the bone to be fixed, so that the segments have sufficient fixation strength while avoiding critical stress concentrations due to an exceedingly stiff implant.

In embodiments of the present invention, osteosynthesis splints, or portions thereof, may be made, for example, of a malleable material, such as medical grade titanium (Ti6Al4V) or stainless steel (316L). In an embodiment of the present invention, an osteosynthesis splint may be constructed of a material being sufficiently malleable to allow for perioperative adjustment to conform the splint to a particular bone geometry. In embodiments of the present invention, osteosynthesis splints may be unitary (constructed of one piece of material), or may be multi-part, connected or bonded in any suitable manner.

In embodiments of the present invention, osteosynthesis splints may be permanent or removable.

Figure 8A:
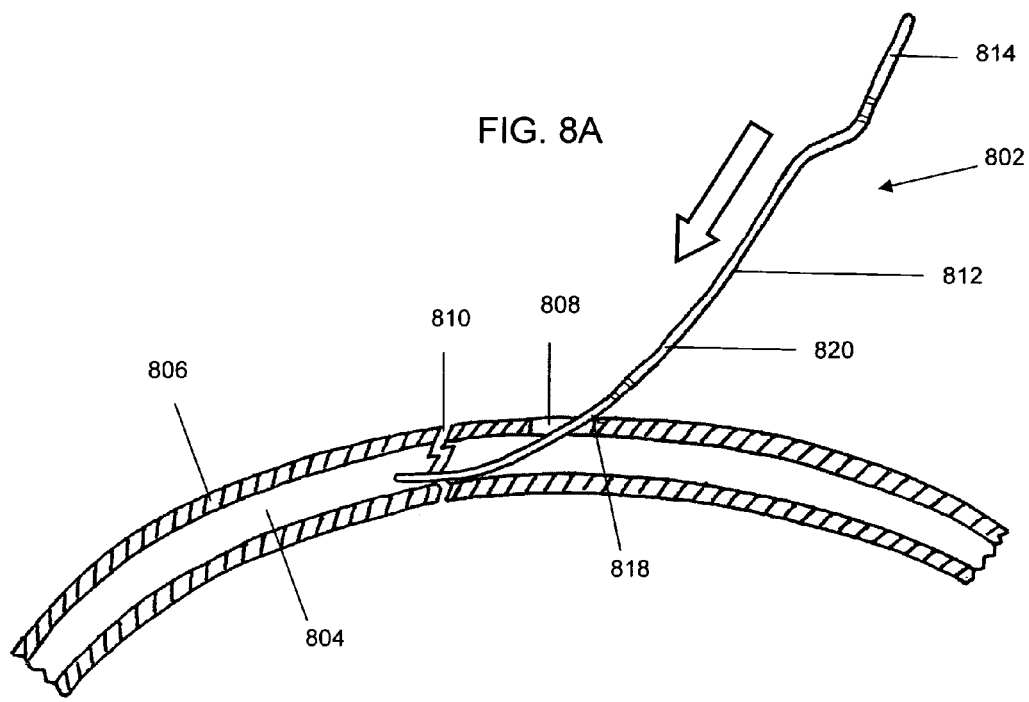
FIGS. 8A, 8B, and 8C illustrate a method of insertion of an apparatus for fixation of bone in accordance with various embodiments of the present invention.
Figure 8B:
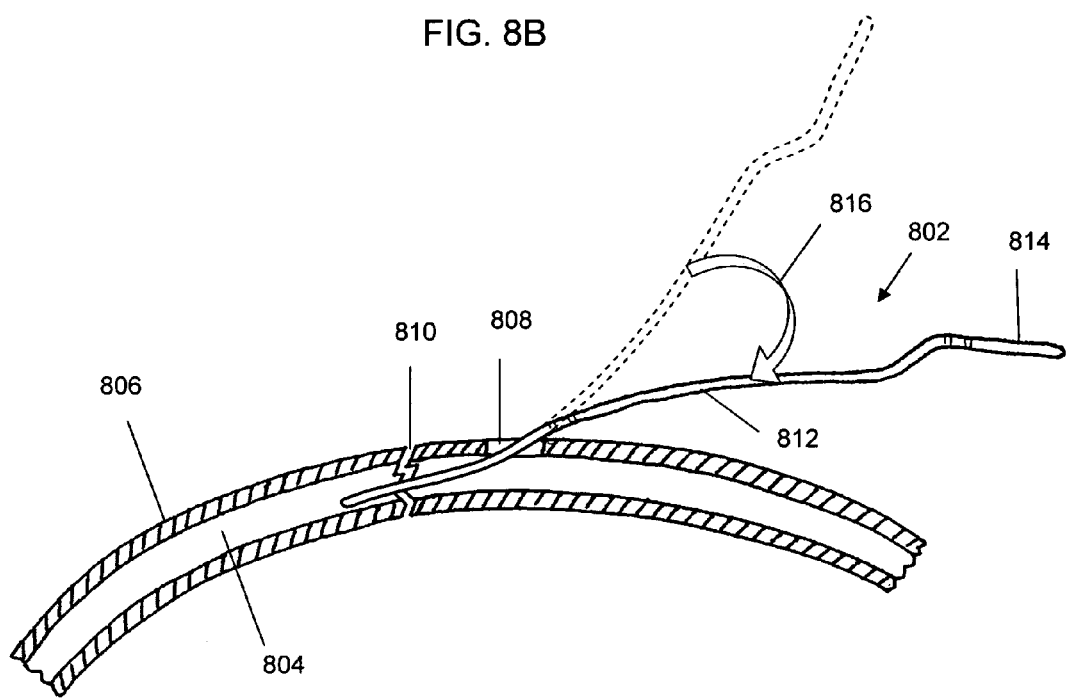
Figure 8C:
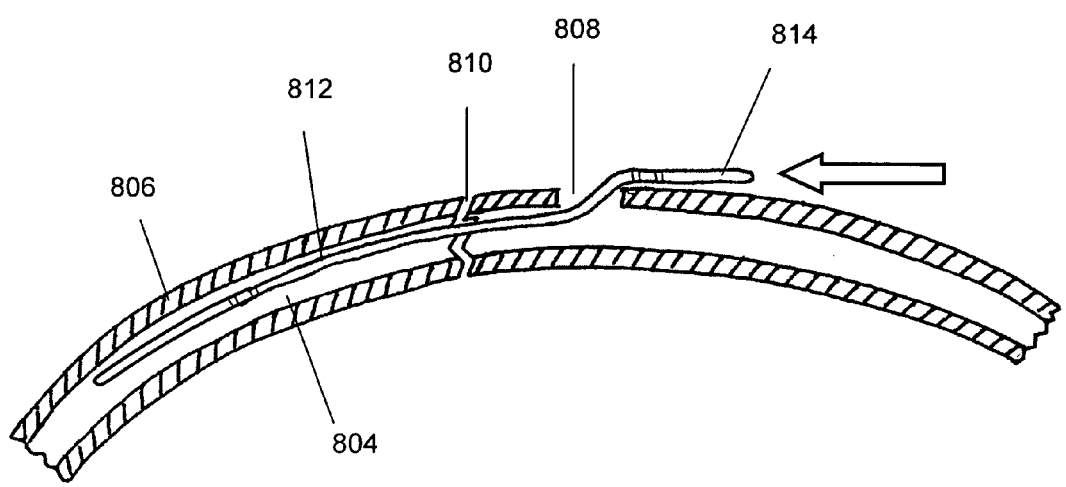

Osteosynthesis splints according to embodiments of the present invention may be used in methods of fixing bones, such as rib bones. FIGS. 8A, 8B, and 8C illustrate an exemplary method in accordance with an embodiment of the present invention.

An osteosynthesis splint 802 may be inserted into intramedullary canal 804 of bone 806, such as a rib bone, through insertion hole 808, which is present or has been formed, for example by drilling into the outer cortex of bone 806, in proximity to fracture site 810.

In an embodiment of the present invention, hole 808 may be created approximately 10-40 mm, for example 20-30 mm, away from fracture site 810. In an embodiment of the present invention, hole 808 may be created with any suitable size to permit insertion of an osteosynthesis splint. For example, in an embodiment of the present invention, hole 808 may be about 1-4 mm, for example 2 mm, larger than the splint to be inserted. Hole 808 may be created in a variety of shapes including circular, oval, elliptical, rectangular, etc.

Alternatively, osteosynthesis splint 802 may be inserted at fracture site 810, directly into intramedullary canal 804, with an exemplary result of such an insertion shown, for example, in FIG. 5.

As shown in FIG. 8B, splint 802 may be partially inserted into intramedullary canal 804, and axially rotated (rotated about the longitudinal axis of splint 802) to align the curvature of splint 802 with the curvature of bone 806 (as shown by arrow 816). In an embodiment of the present invention, splint 802 may be rotated approximately 180°.

Upon complete insertion of intramedullary segment 812 into intramedullary canal 804, plate segment 814 may be attached to the outer surface of bone 806.

In an embodiment of the present invention, an osteosynthesis splint 802 may be inserted into intramedullary canal 804 through an insertion hole 808. To facilitate insertion of splint 802 through insertion hole 808, the width of distal segment 818 of intramedullary segment 812 may be less than the width of proximal segment 820 (see, for example, FIG. 7).

In an embodiment of the present invention, osteosynthesis splint 802 may have a longitudinal curvature along all, or a portion of splint 802, as shown, for example, in distal segment 818 in FIG. 8A. In an embodiment of the present invention, if a longitudinal curvature is present in splint 802, insertion may be initiated with the curvature of the splint opposing the curvature of bone 806. After distal segment 818 has been inserted, osteosynthesis splint 802 may be rotated to align its curvature with that of bone 806, such as the curvature of a rib bone. Subsequent to curvature alignment, intramedullary segment 812 of osteosynthesis splint 802 may be completely inserted along intramedullary canal 804 of bone 806 (see FIG. 8C).

In an embodiment of the present invention, distal segment 818 may be sufficiently flexible to allow distal segment 818 to flex upon contact with a wall of intramedullary canal 804 to facilitate insertion of intramedullary segment 812. Distal segment 818 may be flexible regardless of whether all, or a portion of, intramedullary segment is curved.

In an embodiment of the present invention, without utilizing a curved splint, a flexible splint, and/or a splint having a distal segment with a reduced width, a larger entry hole may be needed to ensure complete insertion of an osteosynthesis splint, whether being inserted into a straight or curved bone. Thus, the present invention provides various mechanisms that may be used alone or in combination to ensure simple and complete insertion of an osteosynthesis splint into a bone.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. An osteosynthesis splint for fixing a rib comprising:
a securing plate segment having a top surface that faces a first direction and an opposed bone securing surface to be placed against a bone, the bone securing surface spaced from the top surface in a second direction that is opposite the first direction;
a transition segment that extends from the securing plate, the transition segment having a proximal end that is coupled to the securing plate, and a distal end that is offset from the proximal end along the second direction;
an intramedullary segment elongate along a longitudinal direction, the intramedullary segment having a proximal segment that extends from the distal end of the transition segment, the intramedullary segment further having a distal segment that extends from the proximal segment such that the proximal segment is disposed between the distal segment and the transition segment, and the intramedullary segment having a top surface that faces the first direction and an opposed bottom surface that faces the second direction, wherein the bottom surface defines a concavity and is devoid of any portion that defines a convexity; and
a central axis that extends along the securing plate, the transition segment, and the intramedullary segment, the central axis lying in a plane that is defined by the first and second directions, and the longitudinal direction.

2. The osteosynthesis splint of claim 1, wherein the distal segment has a first uniform width and the proximal segment has a second uniform width, said first width being less than said second width, wherein the intramedullary segment defines a thickness extending between the top surface and the bottom surface of the intramedullary segment and measured in the first direction, and the second width is greater than the thickness.

3. The splint of claim 2, wherein said transition segment is inclined upwardly from the intramedullary segment to the securing plate segment.

4. The splint of claim 2, wherein the top surface of the securing plate segment defines a first plane, the bone securing surface defines a second plane, and no portion of the intramedullary segment intersects either of the first and second planes.

5. The splint of claim 2, wherein said securing plate segment comprises one or more securing engagements for engaging one or more fasteners.

6. The splint of claim 2, wherein said securing plate segment comprises a notch in one or both opposing lateral edges of said securing plate segment.

7. The splint of claim 2, wherein said proximal segment comprises a substantially rectangular cross section.

8. The splint of claim 2, wherein said proximal segment possesses a higher degree of vertical flexibility than lateral flexibility.

9. The splint of claim 2, further comprising a plurality of securing engagements for engaging one or more fasteners, wherein said intramedullary segment is located distally of all securing engagements.

10. The splint of claim 2, wherein the proximal segment has a width to thickness ratio of about 1.5:1 or greater.

11. The splint of claim 2, wherein the distal segment has a width to thickness ratio that is less than the width to thickness ratio of the proximal segment.

12. The splint of claim 1, wherein the transition segment comprises a concaved bottom surface portion.

13. The splint of claim 12, wherein the top surface of the securing plate segment defines a first plane, the bone securing surface defines a second plane, and no portion of the intramedullary segment intersects either of the first and second planes.

14. The splint of claim 12, wherein said bottom surface of said intramedullary segment defines a radius of curvature of about 5 to about 30 cm, and the radius of curvature is located at a point beneath said bottom surface.

15. The splint of claim 12, wherein the securing plate segment comprises one or more securing engagements for engaging one or more fasteners.

16. The splint of claim 12, wherein the securing plate segment comprises a notch in one or both opposing lateral edges of the securing plate segment.

17. The splint of claim 12, wherein the proximal segment comprises a substantially rectangular cross section.

18. The splint of claim 12, wherein the proximal segment possesses a higher degree of vertical flexibility than lateral flexibility.

19. The splint of claim 1, further comprising a plurality of securing engagements for engaging one or more fasteners, wherein said intramedullary segment is located distally of all securing engagements.

20. The splint of claim 1, wherein the proximal segment has a width to thickness ratio of about 1.5:1 or greater.

21. The splint of claim 1, wherein the distal segment has a width to thickness ratio that is less than the width to thickness ratio of the proximal segment.

22. The splint of claim 1, wherein the intramedullary segment has a length that extends from the transition segment to an end of the distal segment, wherein the bottom surface of the intramedullary segment extends along an entirety of the length and an entirety of the bottom surface is concave in shape.

23. An osteosynthesis splint configured to fix a rib, the splint comprising:
a securing plate segment having a top surface that faces a first direction and an opposed bone securing surface configured to be placed against a bone, the top surface defining a first plane and the bottom surface defining a second plane, the first direction being substantially normal to the first and second planes;
an intramedullary segment coupled to the securing plate segment such that no portion of the intramedullary segment intersects either of the first and second planes, the intramedullary segment having a distal segment, a proximal segment located proximally relative to the distal segment, and a length that extends from the proximal segment away from the securing plate segment and toward the distal segment, and the intramedullary segment having a top surface that faces in the first direction and an opposed bottom surface;

wherein when the intramedullary segment is in a neutral state: (1) at least a portion of the bottom surface is concave in shape along the length of the intramedullary segment; and (2) both the distal segment and the proximal segment are devoid of a first location on the top surface that is closer to the second plane than a second location on the top surface, the second location being located proximally relative to the first location.

24. The splint of claim 23, wherein the bone securing surface is spaced from the top surface in a second direction that is opposite the first direction, and the splint further comprises a transition segment that extends from the securing plate, the transition segment having a proximal end that is coupled to the securing plate, and a distal end that is offset from the proximal end along the second direction, and the opposed bottom surface of the intramedullary segment faces the second direction and defines a concavity.

25. The splint of claim 24, wherein the intramedullary segment is elongate along a longitudinal direction, the splint further comprising a central axis that extends along the securing plate, the transition segment, and the intramedullary segment, the central axis lying in a plane that is defined by the first and second directions, and the longitudinal direction.

26. The splint of claim 23, wherein the intramedullary segment further comprises a tapered segment that extends between the proximal segment and the distal segment.

* * * * *